(12) United States Patent
Hu et al.

(10) Patent No.: US 10,209,095 B2
(45) Date of Patent: Feb. 19, 2019

(54) EDDY CURRENT SENSOR

(71) Applicant: Gree Green Refrigeration Technology Center Co., Ltd. of Zhuhai, Zhuhai (CN)

(72) Inventors: Yusheng Hu, Zhuhai (CN); Weicai Huang, Zhuhai (CN); Jiqing Geng, Zhuhai (CN); Zhichang Liu, Zhuhai (CN)

(73) Assignee: Gree Green Refrigeration Technology Center Co., Ltd. of Zhuhai, Zhuhai (CN)

( * ) Notice: Subject to any disclaimer, the term of this patent is extended or adjusted under 35 U.S.C. 154(b) by 0 days.

(21) Appl. No.: 15/514,981

(22) PCT Filed: Jul. 6, 2015

(86) PCT No.: PCT/CN2015/083398
§ 371 (c)(1),
(2) Date: Mar. 28, 2017

(87) PCT Pub. No.: WO2016/086662
PCT Pub. Date: Jun. 9, 2016

(65) Prior Publication Data
US 2017/0211948 A1 Jul. 27, 2017

(30) Foreign Application Priority Data
Dec. 4, 2014 (CN) .......................... 2014 1 0738356

(51) Int. Cl.
*G01D 5/14* (2006.01)
*G01B 7/02* (2006.01)
(Continued)

(52) U.S. Cl.
CPC ................ *G01D 5/14* (2013.01); *B60L 13/10* (2013.01); *G01B 7/023* (2013.01); *G01N 27/90* (2013.01); *G01N 27/904* (2013.01)

(58) Field of Classification Search
CPC .................................. G01D 5/14; G01B 7/023
See application file for complete search history.

(56) References Cited

U.S. PATENT DOCUMENTS

| 4,392,523 A | * | 7/1983 | Beller | .................. | G01F 23/284 |
| | | | | | 164/450.1 |
| 5,509,310 A | * | 4/1996 | El-Ibiary | ................ | G01B 7/312 |
| | | | | | 340/682 |

(Continued)

FOREIGN PATENT DOCUMENTS

| CN | 1800773 A | 7/2006 |
| CN | 1987367 A | 6/2007 |

(Continued)

*Primary Examiner* — Huy Q Phan
*Assistant Examiner* — Zannatul Ferdous
(74) *Attorney, Agent, or Firm* — The Webb Law Firm

(57) ABSTRACT

The present invention provides an eddy current sensor, comprising: a housing; a plurality of probes which are all disposed inside the housing, probing ends of the probes being all disposed at inner side of an exterior surface of the housing to avoid the probing ends of the probes from protruding out of the exterior surface of the housing. Because the probing ends of the plurality of probes are all located at the inner side of the exterior surface of the housing, the housing will protect the probes when the eddy current sensor is hit by an external force, thereby avoiding damage of the probes due to the impact, which reduces fault rate of the probes, enhances use reliability of the eddy current sensor, and prolongs service life of the eddy current sensor.

12 Claims, 3 Drawing Sheets

(51) Int. Cl.
*B60L 13/10* (2006.01)
*G01N 27/90* (2006.01)

(56) References Cited

U.S. PATENT DOCUMENTS

| | | | |
|---|---|---|---|
| 7,295,004 B2 * | 11/2007 | Kroner | G01N 27/9033 |
| | | | 324/220 |
| 2004/0178790 A1 * | 9/2004 | Gifford | G01N 27/904 |
| | | | 324/242 |
| 2008/0111541 A1 | 5/2008 | Miller | |
| 2008/0271548 A1 * | 11/2008 | Janz | G01D 11/30 |
| | | | 73/866.5 |
| 2011/0304328 A1 | 12/2011 | Yamamoto | |
| 2012/0316419 A1 * | 12/2012 | Chevalier | A61B 5/02007 |
| | | | 600/381 |
| 2013/0002275 A1 * | 1/2013 | Min | G01R 35/005 |
| | | | 324/750.02 |
| 2014/0159709 A1 | 6/2014 | Lin et al. | |

FOREIGN PATENT DOCUMENTS

| | | |
|---|---|---|
| CN | 101920470 A | 12/2010 |
| CN | 102501137 A | 6/2012 |
| CN | 102829709 A | 12/2012 |
| CN | 104154853 A | 11/2014 |
| CN | 204240938 U | 4/2015 |
| CN | 204388770 U | 6/2015 |
| JP | 200617536 A | 1/2006 |

* cited by examiner

EDDY CURRENT SENSOR

CROSS-REFERENCE TO RELATED APPLICATIONS

This application is the United States national phase of International Application No. PCT/CN2015/083398 filed Jul. 6, 2015, and claims priority to Chinese Patent Application No. 201410738356.5 filed Dec. 4, 2014, the disclosures of which are hereby incorporated in their entirety by reference.

FIELD OF THE INVENTION

The present application relates to the technical field of test sensors, and more specifically to an eddy current sensor.

BACKGROUND OF THE INVENTION

The eddy current sensor in the prior art, specifically an integrated eddy current sensor, may be applied to monitoring a motion state of a maglev motor main shaft.

In the prior art, when monitoring a motion state of a maglev motor main shaft, an eddy current displacement sensor is mainly adopted for real-time detection. The precision and stability of the eddy current displacement sensor have a direct impact on the efficiency and reliability of the maglev motor.

The eddy current sensors applied to maglev motors in the current market prevalently have the following problems:

1. Probes mostly protrude outside a housing of the eddy current sensor; therefore, the housing of the eddy current sensor has little protection effect to the probe, which easily causes damage of the probe.

2. No compensation probe is provided on the eddy current sensor; the eddy current sensor is largely affected by environmental temperature and thus cannot be applied to places with a severe environment such as high temperature and high pressure.

3. A proximitor (control and processing circuits of the sensor) is mostly integrated into a housing of the eddy current sensor, which has a higher requirement on temperature stability and pressure stability of the control circuit components.

SUMMARY OF THE INVENTION

A main objective of the present application is to provide an eddy current sensor to solve the problems in the prior art such as easy damage of a probe and short service life of the sensor caused by protruding the probe out of an exterior surface of a housing.

In order to achieve the objective above, the present application provides an eddy current sensor, comprising: a housing; a plurality of probes which are all disposed inside the housing, probing ends of the probes being all disposed at inner side of an exterior surface of the housing to avoid the probing ends of the probes from protruding out of the exterior surface of the housing.

Further, the plurality of probes include a plurality of radial probes; the housing has an inner annular face having radial probing holes to avoid the radial probes, probing ends of the radial probes being disposed corresponding to the radial probing holes, and the probing ends of the radial probes being tangent with the inner annular face.

Further, the housing is of an annular structure; an annular groove is provided inside the housing; an inner wall of the housing is formed between an inner groove wall of the annular groove and the inner annular face of the housing; the inner wall has a radial probing hole disposed therethrough along a radial direction of the housing.

Further, an exterior wall of the housing is formed between an exterior groove wall of the annular groove and an exterior annular face of the housing, the exterior wall having a via-hole disposed therethrough along an axial direction of the radial probing hole.

Further, an exterior wall of the housing is formed between an exterior groove wall of the annular groove and an exterior annular face of the housing, the exterior wall also having a via-opening in communication with the annular groove.

Further, the eddy current sensor also comprises a filler element that fills interstices inside the housing to form the housing into a solid annular cylindrical body.

Further, a plurality of probes include at least one axial probe, and the housing has an inner annular face and a radial end face perpendicular to the inner annular face, a probing end of the axial probe being flush with the radial end face of the housing.

Further, the plurality of probes include: a plurality of radial probes equidistantly arranged along a circumference of the housing; one axial probe disposed on a perpendicular bisector of a connecting line of two adjacent radial probes.

Further, the eddy current sensor further comprises a proximitor that is electrically connected to the probes, the proximitor being external to and separating from the housing.

Further, the plurality of probes further include: a metal piece disposed on the housing in contact with an ambient environment; a compensation probe, a probing end of which is disposed on the metal piece.

Further, the eddy current sensor further comprises a range adjusting part via which the probing end of the compensation probe contacts the metal piece.

Further, the housing is of an annular structure; an annular groove is provided inside the housing; the housing also has a stepped hole disposed through a groove bottom of the annular groove; a hole diameter of a part proximate to the annular groove of the stepped hole is larger than a hole diameter of a part far from the annular groove of the stepped hole; the compensation probe and the metal piece are provided inside the stepped hole; and the metal piece is stopped at a stepped face of the stepped hole.

Further, the metal piece is made of a same material as a detected rotary shaft.

According to the technical solution of the present application, a plurality of probes are disposed inside the housing; moreover, the probing ends of the probes are all disposed at the inner side of the exterior surface of the housing. Because the probing ends of the plurality of probes are all located at the inner side of the exterior surface of the housing, the housing will protect the probes when the eddy current sensor is hit by an external force, thereby avoiding damage of the probes due to the impact, which reduces fault rate of the probes, enhances use reliability of the eddy current sensor, and prolongs service life of the eddy current sensor.

BRIEF DESCRIPTION OF THE ACCOMPANYING DRAWINGS

The drawings illustrated here are for providing further understanding of the present application and thus constitute part of the present application. The exemplary embodiments of the present application and depictions thereof are for interpreting the present application, not constituting improper limitations of the present application. In the drawings.

Reference Numerals in the Drawings

Figure 1:
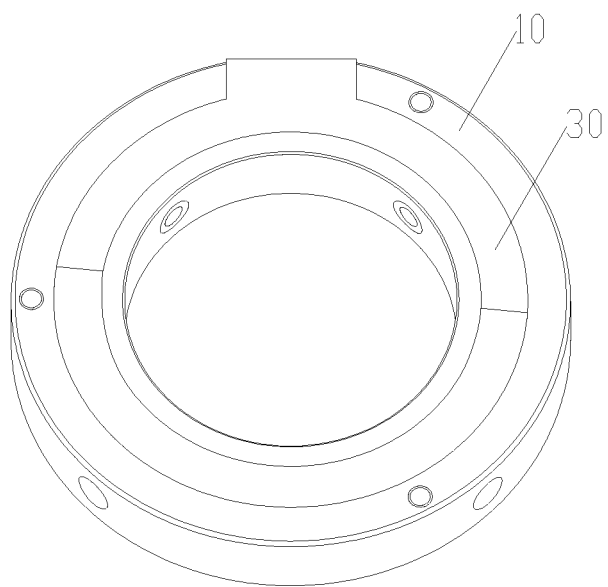
FIG. 1 is a structural diagram of an eddy current sensor in the present application.

10. Housing; 11. Inner annular face; 11a. Radial probing hole; 12. Annular groove; 12a. Inner groove wall; 12b. Exterior groove wall; 12c. Groove bottom; 13. Inner wall; 14. Exterior annular face; 15. Exterior wall; 15a. Via-hole; 15b. Via-opening; 16. Radial end face; 17. Stepped hole; 17a. Stepped face; 20. Radial probe; 30. Filler element; 40. Axial probe; 50. Metal piece; 60. Compensation probe; 70. Range adjusting part; 80. Rotary shaft.

DETAILED DESCRIPTION OF THE PREFERRED EMBODIMENTS

It should be noted that without conflicts, embodiments of the present application and the features in the embodiments may be mutually combined. Hereinafter, the present application will be described in detail with reference to the accompanying drawings in conjunction with the embodiments.

The present application provides an eddy current sensor. As shown in FIGS. 1-6, the eddy current sensor comprises a housing 10 and a plurality of probes which are all disposed inside the housing 10. Probing ends of the probes are all disposed at inner side of an exterior surface of the housing 10, such that the housing 10 will protect the probes when the eddy current sensor is hit by an external force, thereby avoiding damage of the probes due to the impact, which reduces fault rate of the probes, enhances use reliability of the eddy current sensor, and prolongs service life of the eddy current sensor.

Preferably, the housing 10 is made of weakly magnetic conductive aluminum alloy or stainless steel. The housing 10 made of weakly magnetic conductive aluminum alloy or stainless steel may effectively reduce interference with a probe vortex field from a strongly magnetic conductive metal housing, thereby enhancing testing precision.

The plurality of the probes in the present application include a plurality of radial probes 20. The housing 10 has an inner annular face 11 having radial probing holes 11a to avoid the radial probes 20, and probing ends of the radial probes 20 are disposed corresponding to the radial probing holes 11a. The probing ends of the radial probes 20 are tangent with the inner annular face 11 (See FIG. 2 and FIG. 3), thereby ensuring testing precision of the radial probe 20 while protecting the radial probes 20 by the inner annular face 11, which avoids decrease of the testing precision caused by the radial probes 20 disposed too deep inside the housing 10.

Figure 2:
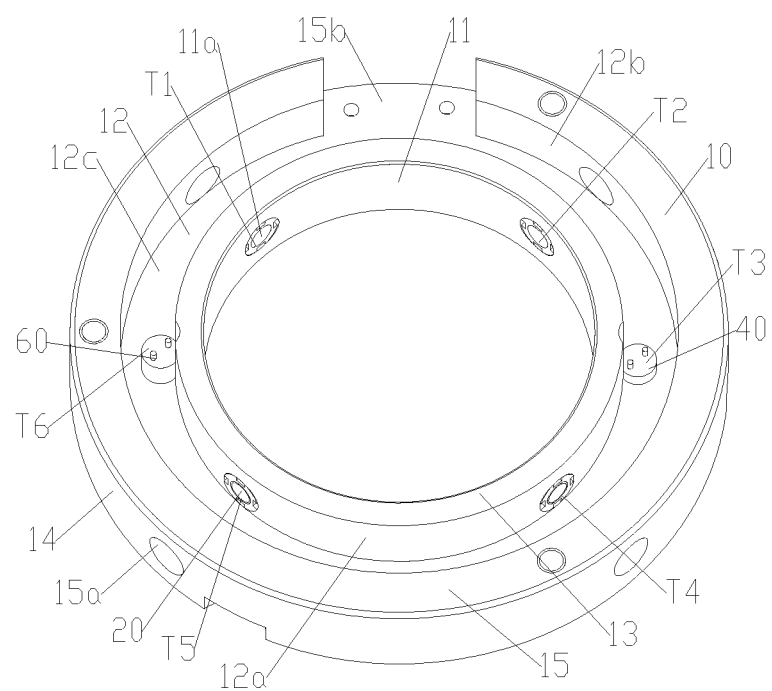
FIG. 2 is a schematic diagram showing a mounting relationship between a housing and probes in the present application.
Figure 3:
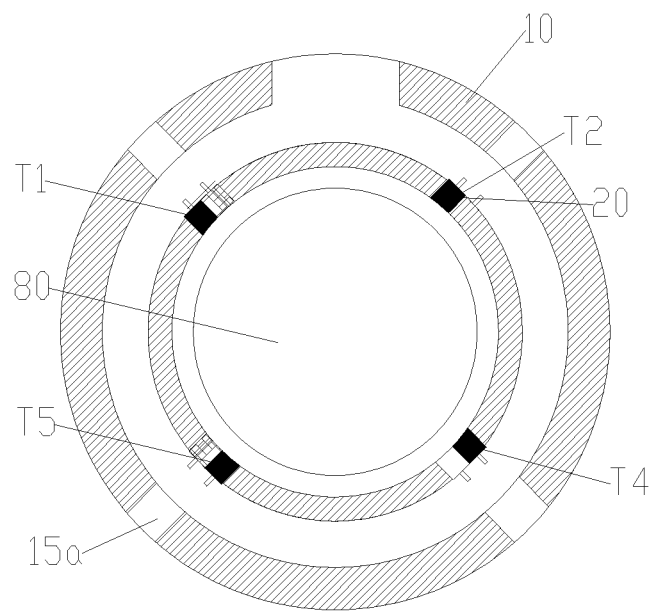
FIG. 3 is a schematic diagram showing a mounting relationship between a housing and radial probes in the present application.

In a preferred embodiment shown in FIGS. 1-3, the housing 10 is of an annular structure; an annular groove 12 is provided inside the housing 10; an inner wall 13 of the housing is formed between an inner groove wall 12a of the annular groove 12 and the inner annular face 11 of the housing 10; the inner side wall 13 has a radial probing hole 11a disposed therethrough along a radial direction of the housing 10. Because the inner side wall 13 has a radial probing hole 11a disposed therethrough along a radial direction of the housing 10, after the radial probe is mounted inside the radial probing hole 11a, stability of mounting the radial probe 20 can be guaranteed, thereby guaranteeing testing accuracy of the eddy current sensor.

In a preferred embodiment shown in FIGS. 1-3, an exterior wall 15 of the housing 10 is formed between an exterior groove wall 12b of the annular groove 12 and an exterior annular face 14 of the housing 10, the exterior wall 15 having a via-hole 15a disposed therethrough along an axial direction of the radial probing hole 11a. Because the via-hole 15a is provided at the exterior wall 15 of the housing 10, a signal line connected to the radial probe 20 may be passed through the via-hole 15a to outside of the housing 10. Because the via-hole 15a and the radial probing hole 11a are co-axially disposed, it may be guaranteed that the signal line may be passed to outside of the housing 10 with a shortest distance, thereby reducing consumption of the signal line and then lowering the manufacture cost of the eddy current sensor.

In the present application, an exterior wall 15 of the housing 10 is formed between an exterior groove wall 12b of the annular groove 12 and an exterior annular face 14 of the housing 10, the exterior wall 15 also having a via-opening 15b in communication with the annular groove 12 (see FIG. 2 and FIG. 3). Due to providing of the via-opening 15b, the signal line connected to the probes may also be passed through the via-opening 15b to outside of the housing 10, thereby ensuring signal transmission reliability of the eddy current sensor.

As illustrated in FIG. 1, the eddy current sensor also comprises a filler element 30 that fills interstices inside the housing 10 to form the housing 10 into a solid annular cylindrical body. Preferably, the housing 10 may be integrally encapsulated by plastic with the probes. Because the filler element 30 is used to fill the interstice inside the housing 10, the probes may be fixed within the housing 10, thereby guaranteeing mounting stability of the probes while ensuring stability of detecting the eddy current sensor. Preferably, the filler element 30 is made of plastic. Air inside the housing 10 and respective welding points on the probes are all integrally encapsulated by plastic with molds. Encapsulating may fill the interstices inside the housing 10, thereby enhancing usage reliability of the eddy current sensor. Because the housing 10, respective probes, cables, and joints of the eddy current sensors encapsulated by plastic become integral, testing stability and signal transmission stability of the eddy current sensor may be significantly improved.

The plurality of probes in the present application include at least one axial probe 40, and the housing 10 has an inner annular face 11 and a radial end face 16 perpendicular to the inner annular face 11, a probing end of the axial probe 40 being flush with the radial end face 16 of the housing 10. Due to providing of the axial probe 40, axial motion state of the detected rotary shaft 80 may be detected in real time, thereby guaranteeing versatility and comprehensiveness of the eddy current sensor at detection.

Figure 4:
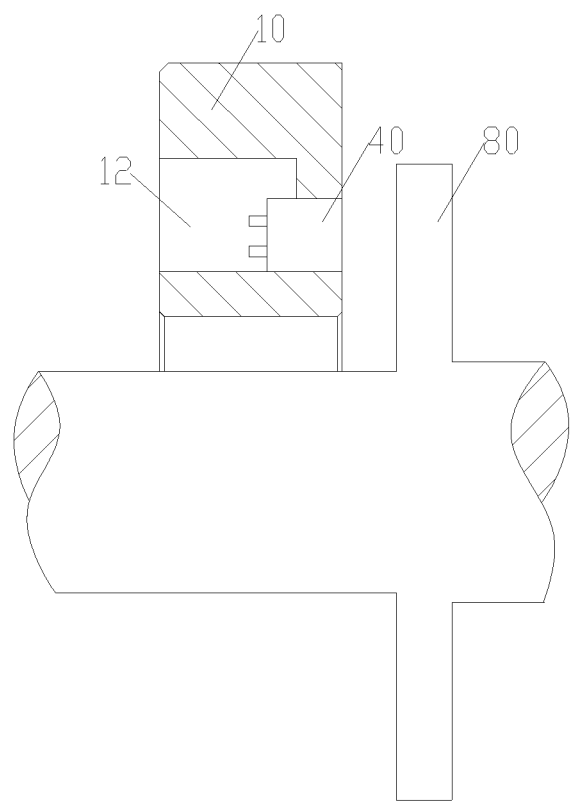
FIG. 4 is a schematic diagram showing a mounting relationship between a housing and an axial probe in the present application.

In a preferred embodiment of FIG. 4, the probing end of the axial probe 40 is flush with the radial end face 16 of the housing 10, which can effectively guarantee testing precision of the axial probe 40. In the preferred embodiment, the axial probe 40 is disposed within the annular groove 12; moreover, the groove bottom 12c of the annular groove 12 has an axial mounting hole disposed therethrough, and the axial probe 40 is disposed within the axial mounting hole.

In the present application, the plurality of probes include: a plurality of radial probes 20 equidistantly arranged along a circumference of the housing 10; one axial probe 40 disposed on a perpendicular bisector of a connecting line of two adjacent radial probes 20. That is, a distance between the axial probe 40 and one of two adjacent radial probes 20 is equal to a distance between the axial probe 40 and the other radial probe 20. Equidistantly arranging of the plurality of radial probes 20 about the housing 10 can effectively guarantee reliability of radial detection. Disposing of the axial probe 40 on a perpendicular bisector of a connecting line of two adjacent radial probes 20 can effective eliminate mutual interface between two radial probes 20 and avoid testing error caused by biasing of the axial probe 40, thereby ensuring detecting precision of the eddy current sensor.

Preferably, one axial probe 40 can satisfy testing requirements; of course, a plurality of axial probes 40 may be provided.

In a preferred embodiment shown in FIG. 4, there are provided four radial probes 20; two adjacent radial probes assume an included angle of 90°. Of course, 6 or 8 radial probes may also be selected.

In the present application, the eddy current sensor further comprises a proximitor that is electrically connected to the probes, the proximitor being external to and separating from the housing 10. Because the proximitor is external to and separates from the housing 10, the proximitor may be made as far as possible away from the testing environment, which avoids respective components of the proximitor from being affected by use environment (pressure field, temperature field, electromagnetic field, vibration field, etc.), thereby enhancing detection precision and reliability of the eddy current sensor. Meanwhile, the size of the eddy current sensor may also be reduced.

Preferably, the proximitor comprises control and processing circuitry of the sensor. Further, the proximitor is mounted on a main control board or disposed separately.

Figure 5:
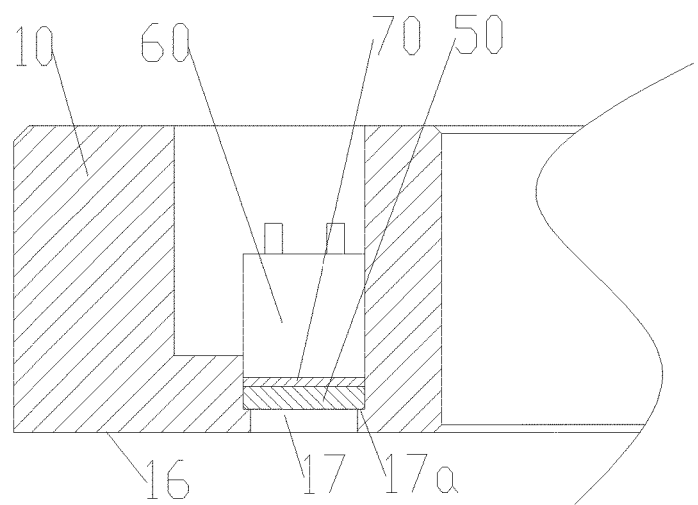
FIG. 5 is a schematic diagram showing a mounting relationship between a housing and a compensation probe in the present application.

Preferably, the plurality of probes further include: a metal piece 50 disposed on the housing 10 in contact with an ambient environment; and a compensation probe 60, a probing end of which is disposed on the metal piece 50 (see FIG. 5). Because the metal piece 50 is in contact with the ambient environment, the metal piece can sense temperature change of the external environment so as to generate its own deformation, while the compensation probe 60 detects this deformation as a compensation correction amount for the radial probes 20 and axial probe 40. The compensation probe 60 may realize real-time detection of impact of the temperature and pressure changes on probe output signals, thereby compensating testing results of other probes, which reduces the impact of environment factors on testing of the eddy current sensor and effectively enhances the testing accuracy.

Preferably, the compensation probe 60 is also an eddy current probe.

Further, the metal piece 50 is a metal gasket.

Preferably, the metal piece 50 is made of a same material as a detected rotary shaft 80.

In the present application, the eddy current sensor also comprises a range adjusting part 70 via which the probing end of the compensation probe contacts the metal piece 50. Due to disposing of the range adjusting part 70, the testing range of the compensation probe 60 can be adjusted so as to consistent with the range of other probes.

Preferably, the range adjusting part 70 is a plastic gasket. The plastic gasket mainly is configured to locate the compensation probe 60 at a middle range position, because during practical working of the unit, all other probes mainly work at the middle range position. The range adjusting part 70 is configured to raise the compensation probe 60 relative to the radial end face 16.

In a preferred embodiment shown in FIG. 5, the housing 10 is of an annular structure; moreover, an annular groove 12 is provided inside the housing 10; the housing 10 also has a stepped hole 17 disposed through a groove bottom 12c of the annular groove 12; a hole diameter of a part proximate to the annular groove 12 inside the stepped hole 17 is larger than a hole diameter of a part far from the annular groove 12; the compensation probe 60 and the metal piece 50 are provided inside the stepped hole 17; and the metal piece 50 is stopped at a stepped face 17a of the stepped hole 17. Because the compensation probe 60 and the metal piece 50 are provided inside the stepped hole 17 and the metal piece 50 is stopped at a stepped face 17a of the stepped hole 17, mounting stability of the compensation probe 60 and the metal piece 50 are ensured, thereby guaranteeing testing reliability of the eddy current sensor.

Figure 6:
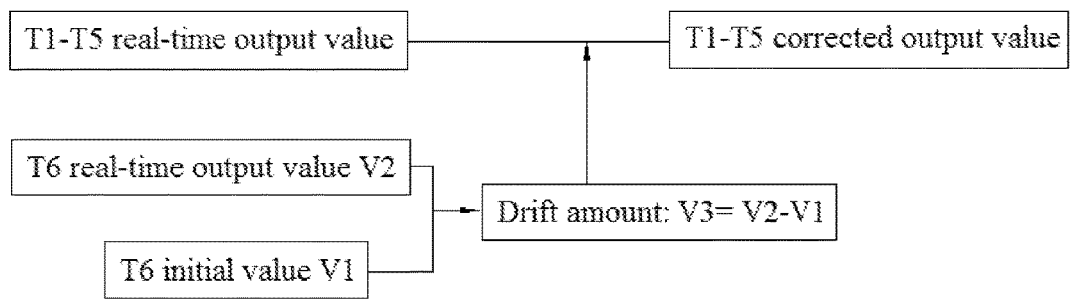
FIG. 6 is a compensation principle diagram of a compensation probe in the present application.

In the preferred embodiments of FIG. 2 and FIG. 6, the four radial probes 20 are labelled as T1, T2, T4, and T5, respectively, wherein T1 and T4 which are symmetrically disposed in 180° may test x-direction displacement of the rotary shaft 80, while T2 and T5 which are symmetrically disposed in 180° may test y-direction displacement of the rotary shaft 80. The axial probe 40 is labelled as T3 and disposed in a middle position between two adjacent radial probes 20, i.e., between T2 and T4. The compensation probe 60 is labelled as T6 and disposed at a middle position between adjacent two radial probes 20, i.e., between T1 and T5. In structural design, the compensation probe 60 detects a constant displacement and theoretically outputs a constant value V1; when temperature and pressure around the eddy current sensor change, an output value of the compensation probe 60 will drift; the value V2 outputted in real time by the compensation probe 60 minus the previous constant value V1 is a drift amount V3, which may be used to perform real-time compensation and correction to output of other probes in the environment.

It may be seen from depictions above that the embodiments of the present application achieve the following technical effects:

1. The eddy current sensor of the present application has characteristics of high testing reliability and high testing precision.

2. The eddy current sensor in the present application has functions of temperature drift compensation and pressure drift compensation, and therefore may be applied in complex testing environments such as high temperature and high pressure.

What have been discussed above are only preferred embodiments of the present application, not for limiting the present application. For those skilled in the art, the present application may have various changes and variations. Any modification, equivalent replacement, improvement within the principle and spirit of the present application should be included within the protection scope of the present application.

The invention claimed is:

1. An eddy current sensor, comprising:
   a housing having an inner side and an exterior surface; and
   a plurality of probes disposed inside the housing, wherein each of the plurality of probes comprises a probing end, and wherein each of the probing ends of the plurality of probes is disposed within the inner side of the housing to avoid the probing ends of the plurality of probes from protruding out of the exterior surface of the housing,
   wherein the housing is an annular structure, and an annular groove is provided inside the housing, wherein an inner wall of the housing is formed between an inner groove wall of the annular groove and an inner annular face of the housing, the inner wall having a radial probing hole disposed therethrough along a radial direction of the housing.

2. The eddy current sensor according to claim 1, wherein the plurality of probes include a plurality of radial probes and the housing has an inner annular face having radial probing holes, wherein the probing ends of the radial probes are disposed within the corresponding radial probing holes, the probing ends of the radial probes being tangent with the inner annular face.

3. The eddy current sensor according to claim 1, wherein an exterior wall of the housing is formed between an exterior groove wall of the annular groove and an exterior annular face of the housing, the exterior wall having a via-hole disposed therethrough along an axial direction of the radial probing hole.

4. The eddy current sensor according to claim 1, wherein an exterior wall of the housing is formed between an exterior groove wall of the annular groove and an exterior annular face of the housing, the exterior wall having a via-opening in communication with the annular groove.

5. The eddy current sensor according to claim 1, wherein the eddy current sensor further comprises a filler element that fills interstices inside the housing to form the housing into a solid annular cylindrical body.

6. The eddy current sensor according to claim 1, wherein the plurality of probes include at least one axial probe, and the housing has an inner annular face and a radial end face perpendicular to the inner annular face, a probing end of the axial probe being flush with the radial end face of the housing.

7. The eddy current sensor according to claim 1, wherein the plurality of probes include:
   a plurality of radial probes equidistantly provided along a circumference of the housing; and
   one axial probe disposed on a perpendicular bisector of a connecting line of two adjacent radial probes.

8. The eddy current sensor according to claim 1, wherein the eddy current sensor further comprises a proximitor that is electrically connected to the probes, the proximitor being external to and separate from the housing.

9. The eddy current sensor according to claim 1, wherein the plurality of probes comprise:
   a metal piece disposed on the housing in contact with an ambient environment; and
   a compensation probe having a probing end of which is disposed on the metal piece.

10. The eddy current sensor according to claim 9, wherein the eddy current sensor further comprises a range adjusting part via which the probing end of the compensation probe contacts the metal piece.

11. The eddy current sensor according to claim 9, wherein, the housing is an annular structure; and an annular groove is provided inside the housing; the housing also has a stepped hole disposed through a groove bottom of the annular groove, wherein a hole diameter of a part proximate to the annular groove inside the stepped hole is larger than a hole diameter of a part far from the annular groove; the compensation probe and the metal piece are provided inside the stepped hole; and the metal piece is stopped at a stepped face of the stepped hole.

12. The eddy current sensor according to claim 9, wherein the metal piece is made of a same material as a detected rotary shaft.

* * * * *